United States Patent [19]

Mathis

[11] Patent Number: 6,020,212
[45] Date of Patent: Feb. 1, 2000

[54] PHYCOBILIPROTEIN-LINKER PEPTIDE COMPLEX FLUORESCENT TRACER AND METHODS OF USING THE SAME

[75] Inventor: Gerard Mathis, Bagnols sur Ceze, France

[73] Assignee: CIS Bio International, Saclay, France

[21] Appl. No.: 08/973,364

[22] PCT Filed: Jun. 7, 1996

[86] PCT No.: PCT/FR96/00865

§ 371 Date: Feb. 23, 1998

§ 102(e) Date: Feb. 23, 1998

[87] PCT Pub. No.: WO96/42016

PCT Pub. Date: Dec. 27, 1996

[30] Foreign Application Priority Data

Jun. 9, 1995 [FR] France ................................. 95 06821

[51] Int. Cl.[7] ......................... G01N 33/533; C07K 16/30
[52] U.S. Cl. ........................ 436/546; 436/531; 436/800; 436/813; 530/391.3
[58] Field of Search ..................... 436/546, 519, 436/800, 813, 531; 530/391.3

[56] References Cited

U.S. PATENT DOCUMENTS

| | | | |
|---|---|---|---|
| 4,520,110 | 5/1985 | Stryer et al. | 436/501 |
| 4,542,104 | 9/1985 | Stryer et al. | 436/536 |
| 4,857,474 | 8/1989 | Waterbury et al. | 436/501 |
| 5,457,184 | 10/1995 | Lehn et al. | 534/16 |
| 5,512,493 | 4/1996 | Mathis | 436/537 |

FOREIGN PATENT DOCUMENTS

| | | |
|---|---|---|
| 0 076 695 | 10/1982 | European Pat. Off. . |
| 0 174 744 | 8/1985 | European Pat. Off. . |

OTHER PUBLICATIONS

P. Fuglistaller et al, Biol. Chem. Hoppe–Seyler, vol. 368, pp. 353–367 (1987)., Apr. 1987.

Wolfgang Reuter and Claudia Mickel–Reuter; "Molecular Assembly of the Phycobilisomes from the Cyanobacterium *Mastigocladus laminosus*"; J. Photochem, Photobiol. B: Biol., 18 (1993) 51–66.

Vernon T. Ol, Alexander N. Glazer and Lubert Stryer; "Fluorescent Phycobiliprotein conjugates for Analyses of cells and Molecules," The Journal of Cell Biology, vol. 93, Jun. 1982, pp. 981–986, The Rockefeller University Press.

Alexander N. Glaser; "Light Guides—Directional Energy Transfer in a Photosynthetic Antenna;" Minireview; The Journal of Biological Chemistry, vol. 264, No. 1, Issue of Jan. 5, pp. 1–4, 1989.

*Primary Examiner*—Mary E. Ceperley
*Attorney, Agent, or Firm*—Woodcock Washburn Kurtz Mackiewicz & Norris LLP

[57] ABSTRACT

The use of a phycobiliprotein-linker peptide complex as a fluorescent tracer in a fluorescent method of detecting and/or determining an analyte in a medium in which it may be present, is disclosed. Fluorescent conjugates consisting of said complex covalently bonded to one of the elements of a ligand/receptor specific binding pair, are also disclosed.

29 Claims, No Drawings

PHYCOBILIPROTEIN-LINKER PEPTIDE COMPLEX FLUORESCENT TRACER AND METHODS OF USING THE SAME

The invention relates to the use of a phycobiliprotein-linker peptide complex as a fluorescent tracer, notably in a fluorescent method of detecting and/or determining an analyte in a medium in which it may be present, as well as to the fluorescent conjugates constituted of said complex covalently bound to one of the elements of a ligand/receptor specific binding pair.

The use of immunological determinations in qualitative and quantitative analysis of compounds in biological fluids is currently well known.

Amongst the existing techniques, the determinations by fluorimetry have become of increasing importance.

In fact, they possess a certain number of advantages amongst which are the sensitivity, the speed of measurement, the stability and the innocuousness of the reagents labelled by fluorescent compounds, and the relatively low cost.

The phycobiliproteins are constituents of the phycobilisome of various bacteria, algae or cryptomonads and are in general of four types: the phycocyanines, the phycoerythrins, the phycoerythrocyanines and the allophycocyanines.

The proteins are made up of α and β sub-units, and sometimes γ sub-units, each one having one or more fluorophores, and are isolated mainly as trimers or hexamers.

Some of them are used as fluorescent labelling compounds by virtue of the many advantages they have in terms of quantum yield, absorption bands, stability and solubility (V.Oi et al, J. Cell Biology 1982, 93, 981).

Schematically, phycobilisomes are made up of two parts:
the core made up of cylindrical elements constituted by allophycocyanines; and
rods, made up of cylindrical elements fixed to the c(ore, said elements being constituted by phycoerythrins and phycocyanines.

The rods and cylinders are made up of an assembly of disks of phycobiliproteins. These disks are assembled between themselves as well as the rods to the core and the core to the thylakoid membrane via linker peptides.

These peptides are named according to their lcicalisation in accordance with the publication A. Glazer, J. Biol. Chem., 1989, 264, 1–4:

$L_R$ for linker peptide in the rod $L_C$ for linker peptide in the core $L_{RC}$ for linker peptide in the rod-core $L_{CM}$ for linker peptide in the core-membrane.

The purification of the phycobiliproteins by conventional methods makes it possible to obtain trimeric or hexameric $(\alpha\beta)_3$ or $(\alpha\beta)_6$ complexes which are devoid of linker peptides. The trimers have a disk shape of ≈30 Å thickness and ≈120 Å diameter.

The use of phycobiliproteins, notably allophycocyanine and phycoerythrin, in immunological determinations by fliiorimetry is described notably in EP 0 174 744 and 0 076 695 as well as in the patents U.S. Pat. Nos. 4,520,110 and 4,542,104.

It has been found that under certain conditions of purification of the phycobilisomes, it was possible to obtain phycobil-iprotein-linker peptide complexes (P. Fuglistaller et al., Biol. Chem. Hoppe-Seyler, 1987, 368, 353–367). However, these complexes were hitherto described in the literature as being relatively unstable and sensitive to proteases (W. Reuter and C. Nickel-Reuter, J. Photochem. Photobiol., B: Biol., 1993, 18, 51–66).

Advantageously, it has now been found that these complexes possess spectroscopic particularities with respect to the phycobiliproteins for a use as a fluorescent tracer.

In fact, such a phycobiliprotein-linker pejptide complex always possesses spectroscopic properties which are different from those of the phycobiliprotein alone, generally with:

an increase in quantum yield and/or—a shift of the emission wavelength and/or—a modification of the absorption wavelength and/or—a modification of the molar absorption coefficient with respect to the phycobiliprotein alone.

These properties can reveal to be particularly interesting during the implementation of a detection system which uses one or more fluorescent tracers, in which, in addition to the stability of the tracers in the medium, two parameters are of utmost importance:

the quantum yield, which directly influences the limit of detection of the system, the emission wavelength which, during the use of several tracers, is a determining factor of their choice.

Unexpectedly, it has now been found that:

these phycobiliprotein-linker peptide complexes are stable in solution and in the presence of sera of various origins containing naturally different proteases, it is possible to covalently bind these complexes onto various proteins and antibodies while keeping the fluorescent properties of the complexes.

In an advantageous aspect, the phycobiliprotein used according to the invention is selected from phycoerythrin, phycoerythrocyanine, phycocyanine, allophycocyanine and allophycocyanine B.

In the rest of the description, the following abbreviations will be used to designate the preferred phycobiliproteins:allophycocyanine=AP, phyco-erythrin=PE, phycoerythrocyanine=PEC, phycocyanine=PC, allophyco-cyanine B=APB Preferably, the phycobiliprotein-linker peptide complex is extracted from a cyanobacterium selected from Mastigoclodus Laminosus, Synechocystis 6701, Synechococcus 6301, *Anabaetia iariabilis* and Nostoc spec.

The linker peptide of the complex used for the purposes of the invention is preferably selected from the peptides $L_R$, $L_C$, $L_{RC}$ and $L_{CM}$, such as defined above.

Advantageously, the complexes usable according to the invention are defined in the following manner, from phycobiliproteins such as designated by the abbreviations mentioned above, sub-units α and β and linker peptides mentioned above:

$(\alpha^{PEC}, \beta^{PEC})_6 L_R$, $(\alpha^{PEC}, \beta^{PEC})_3 L_R$, $(\alpha^{PC}, \beta^{PC})_6 L_R$, $(\alpha^{PC}, \beta^{PC})_6 L_{PC}$, $(\alpha^{PC}, \beta^{PC})_3 L_R$, $(\alpha^{AP}, \beta^{AP})_3 L_C$, $(\alpha^{APB}, \alpha_2^{AP}, \beta_3^{AP}) L_C$ and $(\alpha^{AP}, \beta^{AP})_2 L_{CM}$ Advantageously, the phycobiliprotein-linker peptide complexes will be used according to the invention in combination with one or more different fluorescent tracers.

The preferred complex for the purposes of the invention is the $(\alpha^{AP}, \beta^{AP})_3 L_C$ complex, i.e. a phycobiliprotein-linker peptide complex constituted of a trimer of α and β sub-units of allophycocyanine and of the linker peptide in the core.

The length of the peptides varies according to the species and the degradation process during the purification. The length is preferably between 5000 and 30000.

According to a further aspect. the invention also relates to a homogeneous fluorescent method of detecting and/or determining an analyte in a medium in which it may be present, by displaying the product of the reaction between the analyte and at least one corresponding receptor, consisting:

1) in adding, to said medium, a first reagent constituted of at least one receptor of said analyte,
2) in adding a second reagent selected from the analyte or at least one of its receptors, one of the two reagents being coupled with a fluorescent donor compound constituted by a rare earth cryptate, chelate or macrocyclic complex and the other reagent being coupled with a fluorescent acceptor compound, it being possible for the order of addition of the reagents to be the reverse order and, after excitation of the mixture by a source of light at the excitation wavelength of the fluorescent donor compound,
3) in measuring the emission signal fluorescent acceptor compound, characterised in that a phycobiliprotein-linker peptide complex such as defined above is used as fluorescent acceptor compound.

In the present description,

"analyte": defines any substance or group of substances, as well as its or their analogues, that is (are) desired to be detected and/or determined;

"receptor": defines any substance capable of binding specifically to a site of said analyte;

"ligand": defines any substance capable of binding specifically to a receptor.

Rare earth cryptates which can be used in such a determination method as well as in the excess methods and competitive methods described below are notably described in the applications EP 0 180 492, EP 0 232 348, EP 0 321 353 or WO90/04791.

Rare earth macrocyclic complexes bearing N-oxy groups are also described in the application WO93/05049.

These rare earth cryptates and macrocyclic complexes have the advantage of being very stable in proteic and saline media, this property being particularly important in the case of homogeneous immunoassays.

A terbium or europium chelate, cryptate or macrocyclic complex bearing N-oxy groups will preferably be used as fluorescent donor compound in the methods and procedures mentioned in the present description.

According to an advantageous aspect, said method is an excess method consisting 1) in adding, to said medium containing the analyte sought after, a first reagent constituted by at least one receptor of said analyte, coupled with a fluorescent donor compound constituted by a rare earth cryptate, chelate or macrocyclic complex,
2) in adding a second reagent constituted by one or more other receptors of said analyte, said second reagent being coupled with a fluorescent acceptor compound constituted by a phycobiliprotein-linker peptide complex,
3) in incubating said medium after each addition of reagents or after the addition of the two reagents,
4) in exciting the resulting medium at the excitation wavelength of the fluorescent donor compound,
5) in measuring the signal emitted by the fluorescent acceptor compound.

One sole receptor of the analyte can notably be used in said methods which is coupled either with the fluorescent donor compound, or with the fluorescent acceptor compound.

In another aspect of the invention, said method is a competitive method consisting:

1) in adding, to said medium containing the analyte sought after, a first reagent constituted by a receptor of said analyte, coupled with a fluorescent donor compound constituted by a rare earth cryptate, chelate or macrocyclic complex,
2) in adding a second reagent constituted of the analyte coupled with a fluorescent acceptor compound constituted by a phycobiliprotein-liriker peptide complex,
3) in incubating said medium after each addition of reagents or after the addition of the two reagents,
4) in exciting the resulting medium at the excitation wavelength of the fluorescent donor compound,
5) in measuring the signal emitted by the fluorescent acceptor compound.

Advantageously, said homogeneous method using fluorescence to sense and/or determine an analyte in a medium in which it may be present, by displaying the product of the reaction between the analyte and at least one corresponding receptor, is a competitive method consisting:

1) in adding, to said medium containing the analyte sought after, a first reagent constituted by a receptor of said analyte, said receptor being coupled with a fluorescent acceptor compound constituted by a phycobiliprotein-linker peptide complex,
2) in adding a second reagent constituted of the analyte coupled with a fluorescent donor compound constituted by a rare earth cryptate or chelate,
3) in incubating said medium either after the addition of each reagent, or after the addition of the two reagents,
4) in exciting the resulting medium at the excitation wavelength of the fluorescent donor compound,
5) in measuring the signal emitted by the fluorescent acceptor compound.

In a preferred aspect of the methods mentioned above, the first reagent and the second reagent are added simultaneously to the medium containing the analyte sought after.

In a particularly advantageous aspect according to the invention, the fluorescent donor compound used in the methods mentioned above is a chelate, a cryptate or a macrocyclic complex of $Eu^{3+}$, and the fluorescent acceptor compound is the $(\alpha^{AP}, \beta^{AP})_3 LC$ complex.

In a further aspect, the invention also relates to the use of a phycobiliprotein-linker peptide complex such as defined above in a method of amplification of the emission signal of a rare earth cryptate or chelate used as fluorescent donor compound in a determination by fluorescence, in which a fluorescent acceptor compound is also used, characteris(ed in that the rare earth cryptate or chelate possesses a low overall quantum yield, and in that the quantum yield of radiative deactivation from the emission level of the rare earth is lower than the quantum yield of the acceptor, said acceptor being constituted by said phycobiliprotein-linker peptide complex.

In another aspect, the invention also relates to a fluorescent conjugate constituted of a phycobiliprotein-linker peptide complex covalently bound to one of the elements of a ligand/receptor specific binding pair.

Said conjugates can particularly be used for sorting the cells and/or analysing the cell surface in a flow cytometry method, such as notably described in Mel. N.Kronic, J. Immunological Methods, 1986, 92, 1–13.

Protein/protein pairs, protein/DNA pairs or even DNA/DNA pairs may notably be cited as examples of ligand/receptor specific binding pairs.

Preferably, the phycobiliprotein used according to the invention is selected from phycoerythrin, phycoerythrocyanine, phycocyanine, allophycocyanine and allophycocyanine B and the linker peptide is selected from the peptides $L_R$, $L_C$, $L_{RC}$ and $L_{CM}$, such as defined above.

Advantageously, the phycobiliprotein-linker peptide complex is selected from the complexes

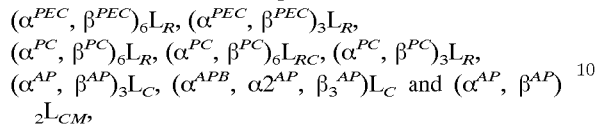

the $(\alpha^{AP}, \beta^{AP})_3 L_C$ complex being preferred.

Preferably, the phycobiliprotein-linker peptide coinplex is extracted from a cyanobacterium selected from Mastigoclodus Laminosus, Synechocystis 6701, Synechococcus 6301, *Anabaena variabilis* and Nostoc spec.

Advantageously, the element of the ligand/receptor specific binding pair is a receptor, in particular a cell receptor or an antibody. Said receptor can, for example, be avidine or streptavidine.

In another advantageous aspect, said element is a ligand, notably an analyte. Said ligand can, for example, be a polypeptide, a lectin or biotin.

EXAMPLE

Carcinoembryonic Antigen (CEA) Determination

A homogeneous immunoassay was carried out using the europium cryptate Eu tris bipyridine diamine as donor compound prepared as described in the application EP 321 353 (examples 3 and 4) coupled to the monoclonal antibody G12 (CIS bio international, France) and either allophycocyanine (Cyanotech, USA), or the $(\alpha^{AP}, \beta^{AP})_3 L_C$ complex as acceptor compound, coupled respectively to the monoclonal antibody G15 (CIS bio international, France).

The abbreviations used below are the following:

AP=allophycocyanine

DTT=dithiotreitrol

EuTBP=Eu trisbipyridine diamine europium cryptate

BSA=bovine serum albumin

HSA=human serum albumin

IgG=immunoglobulin G

SPDP=N-succinimidyl 3(2-pyridyldithio)propionate

Sulpho-SMCC=sulphosuccinimidyl 4-n-maleimidomethyl)cyclohexane

1) PREPARATION OF THE IgG G15-AP CONJUGATES a) Activation of AP by sulpho-SMCC

AP (3 mg), commercially available in a precipitated form in a 60% ammonium sulphate solution, is centrifuged. After removal of the supernatant, the residue is taken up with 250 μl of 100 mM phosphate buffer, pH 7.0, then filtered at 0.8 μm in order to remove any particles in suspension.

The filtrate is purified by exclusion chromatography on a superfine G25 column (Pharmacia, Sweden) in the same buffer. The conce:ntration of AP eluted in the volume of exclusion is determined at 650 nm, in taking an $\epsilon_{650\ nm}$ of 731000$M^{-1}$ $cm^{-1}$ into account.

The activation of AP is carried out by adding a solution of sulpho-SMCC, prepared extemporaneously, at the rate of 6.9 mM in a 100 mM phosphate buffer, pH 7.0, and by allowing the reaction to proceed for an hour at ambient temperature with gentle stirring (molar ratio of 15 to 75 sulpho-SMCC per AP). The AP-maleimide is then purified on a superfine G25 column in 100 mM phosphate buffer, 5 mM EDTA, pH 6.5, and kept at 4° C. before coupling onto the IgG 3D3.

b) Activation of the IgG G15 by SPDP

Simultaneously, 5 mg of IgG G15 at the rate of 10 mg/ml in 100 mM phosphate buffer, pH 7.0, are activated by the additior, of an SPDP solution (Pierce, USA) at the rate of 6.4 mM in dioxan in a molar ratio of 7.5 SPDP per IgG G15.

After 35 minutes of activation at ambient temperature, IgG pyridine-2 thione is purified on a superfine G25 column in a 100 mM phosphate buffer, 5 mM EDTA, pH 6.5.

The proteins are concentrated and the 2-pyridyl disulphide groups are reduced with a solution of DTT (Sigma, USA) having a final concentration of 19 mM for 15 minutes at ambient temperature. The DTT and the pyridine-2-thione are removed by purification on a superfine G25 column in 100 mM phosphate buffer, 5 mM EDTA, pH 6.5. The concentration of IgG-SH is determined at 280 nm with an $\epsilon_{280\ nm}$ of 210000 $M^{-1}$ $cm^{-1}$.

c) Conjugation of the IgG G15-SH with AP-maleimide

The binding of the thiol groups onto the maleimides is carried out by adding 2.51 mg of activated AP per mg of IgG G15-SH. After 18 hours of incubation at 4° C. in the dark with gentle stirring, the thiol functions which have remained free are blocked by the addition of a 100 mM solution of N-methyl maleimide (Sigma, USA) having a final concentration of 20 mM, for one hour at ambient temperature.

The reaction medium is purified by gel filtration on a semi-preparative TSK G3000SW column (Beckmann, USA) in 100 mM phosphate buffer pH 7.0.

The AP and IgG G 15 concentrations in the purified conjugate, eluted in the first peak, are determined by the absorptions at 280 nm and 650 nm, according to the following calculation:

$[AP]_{Mole/1} = A_{650\ nM}/10000$ $[IgG]_{Mole/1} = (A_{280\ nm} - A'_{280\ nm})/210000$ with $A'_{280\ nm}$ being the contribution, at this wavelength, of AP-maleimide, determined above (paragraph 1-a)).

HSA is added at 1 g/l to the conjugate which is then taken as aliquots and then frozen at −20° C.

2) PREPARATION OF THE CONJUGATES IgG G15-$(\alpha^{AP}, \beta^{AP})_3 L_C$ a) Activation of the $(\alpha^{AP}, \beta^{AP})_3 L_C$ complex by sulphio-SMCC.

The $(\alpha^{AP}, \beta^{AP})_3 L_C$ complex is obtained from the alga Masligocladus Laminosus. After extraction of phycobilisomes, the protein-linkcr peptide complexes are purified according to P. Fuglistaller et al. Biol. Chem. Hoppe Seyler 1986, 367, 601–614.

The complexes have the following properties:

$\epsilon_{650} = 1076000$ $M^{-1}$ $cm^{-1}$.

$DO_{650}/DO_{620} = 2.2$.

To 1 ml of $(\alpha^{AP}, \beta^{AP})_3 L_C$ complex at 3 mg/ml in 100 mM phosphate buffer pH 7.0, is added 19.5 μl of a solution of sulpho SMCC (Pierce at 30 mmole/l in the same buffer. Incubation is carried out for 30 minutes at 30° C. The product of the reaction is purified on a G25 HR column 10×10 flow rate 2 ml/min. The fraction eluted in the dead volume is recovered (V=1.7 ml). The $(\alpha^{AP}, \beta^{AP})L_C$ maleimide complex concentration is 1.4 mg/ml.

b) Activation of the IgG G15 by SPDP

The activation is carried out as indicated in point 1, b) above.

c) Conjugation of the IgG G15-SH with the $(\alpha^{AP}, \beta^{AP})_3 L_C$-maleimide complex.

1.7 ml of the solution obtained in point 2, a is placed in contact with 1 ml of the solution of IgG G15-SH at 0.9 mg/ml obtained above.

After incubation for one night at 4° C. with stirrirng with a roller stirrer, the conjugate is purified on a semi-preparative TSK 4000 column (Beckmann, USA) with a flow rate of 4 ml/minute in 100 mM phosphate buffer, pH 7. The fractions of 48 to 64 ml are combined and concentrated on an AMICON cone. The $(\alpha^{AP}, \beta^{AP})_3 L_C$ complex concentration in mg/ml is given by the formula DO650/10.76.

The concentration of IgG in mg/ml is given by the formula $$DO_{280} - \frac{DO_{650}}{5.25} \bigg/ 1.4.$$

The conjugate is at 120 μl/ml IgG with a molar ratio of 1.6 $(\alpha^{AP}, \beta^{AP})_3 L_C$ complex/IgG $DO_{650}/620 = 2.2$.

3) PREPARATION OF THE CONJUGATES IgB G12-Eu TBP

The preparation of IgG G12-SH is carried out according to the protocol described above for the G15 3D3 but by varying the molar raijo from 4 to 16 SPDP per IgG G12.

To 5 mg (5 $10^{-6}$ moles) of Eu TBP is added a 25 mM solution of sulpho-SMCC in 20 mM phosphate buffer, dimethylformamide 10% (v/v pH 7.0 in a proportion of 2.5 moles of activator per mole of Eu TBP.

After 45 minutes' activation at ambient temperature, the reaction medium is filtered at 0.8 μm in order to remove the precipitate which might have formed. The undesirable reaction products (sulpho-SMCC, N-hydroxy-succinimide, (N-maleimidomethyl)carboxylic acid) are removed by ion exchange chromatography on a Mono Q column (Pharnacia, Sweden) in 20 mM phosphate buffer, 10% dimethylformamide (v/v), pH 7.0, under NaCl shock. The Eu TBP maleimide concentration is determined at 307 nm with an $\epsilon_{307\ nm}$ of 25000 $M^{-1}$ cm$^{-1}$ as well as the ratio $A_{307\ nm}/A_{280\ nm}$.

Similar to that described above, the maleimide functions are allowed to react with the thiol functions bound to the antibody in molar proportions varying from 10 to 30 Eu TBP maleimide per IgG G12-SH.

After 18 hours of incubation at 4° C. and blockage of the thiol groups (eventually remained free) by N-methylmaleimide, the non-coupled Eu TBP is removed by a dialysis in 100 mM phosphate buffer, pH 7.0, at 4° C. until depletion (no more fluorescence in the dialysis bath).

The properties of the conjugate are determined by its absorptions at 307 nm and 280 nm by using the following values in taking into account the actual absorption of the cryptate, determined by the ratio $A_{307\ nm}/A_{280\ nm}$.
Eu TBP-maleimide:

$\epsilon_{307\ nm} = 25000\ M^{-1}\ cm^{-1}$ $A_{307\ nm}/A_{280\ nm}$: determined experimentally.
IgG G12-SH:

$\epsilon_{280\ nm} = 210000\ M^{-1}\ cm^{-1}$ $A_{307\ nm} = 0\ M^{-1} cm^{-1}$.

4) APPLICATION TO THE CEA DETERMINATION

The G12-Eu TBP, G15-AP and G15-$(\alpha^{AP}, \beta^{AP})_3 L_C$ complex conjugates are diluted in a 100 mM phosphate buffer, pH 6, BSA 1 g/l, KF 400 mM.

Successively, in polystyrene microplates (Dynatech, USA), are added:

100 μl of standard solution (serum without CEA) or 100 μl of sample to be tested 100 μl of G12-Eu TBP conjugate at 0.5 μg/ml 100 μl of G15-AP conjugate at 5 μg/ml or 100 μl of G15-$(\alpha^{AP}, \beta^{AP})_3 L_C$ complex conjugate.

After incubation for 3 hours at 37° C., the reading is taken with the aid of a laser prototype fluorimeter which is described below:

A nitrogen pulsed laser (LASER SCIENCE INC., model LS1-337ND) is used as excitation source (wavelength at 337.1 nm). The duration of the pulses is specified at 3 nanoseconds and is repeated under a frequency of 10 Hertz. The beam passes through a filter (CORNING) in order to remove any parasite light with an excitation other than 337 nm.

After having entered in the measurement chamber, the beam is reflected by a dichroic filter, placed at 45 degrees, which has the property of reflecting the ultraviolets and being able to transmit visible light.

The beam reflected by the dichroic filter is focused on the measurement wells of a microplate by a lens of molten silica. The emission of fluorescence is collected according to a solid angle of 20 degrees, collimated by the same lens, and passes directly through the dichroic filter (fluorescence in visible light).

An interference filter, the characteristics of which are defined according to the wavelength of fluorescence to be detected, makes it possible to remove the light which may parasite the signal, whose intensity is then measured by a photomultiplier (HAMAMATSU R2949).

The photon counter used is an SR-400 (STANFORD RESEARCH SYSTEMS), whose operations and synchronisation with the laser are controlled by a computer of the type IBM PC-AT via an RS 232 exit. The pulses originating from the photomultiplier are recorded during a time window ($t_g$) and after a delay ($t_d$) determined with the proviso that they be greater than a discriminating level selected by the photon counter in order to optimise the signal/noise ratio of the photomultiplier.

An X-Y table, piloted by IBM PC-AT, allows for the various positions of the measurement microplate by the stepwise motors, including the loading manoeuvres, positioning under the exciting beam, automatic sequential reading of the 96 wells, and exiting.

The fluorescence emitted by the G15-AP or G15-$(\alpha^{AP}, \beta^{AP})_3 L_C$ complex conjugate is measured with the aid of the prototype fluorimeter equipped with a filter at 665 nm of 10 nm length at mid-height, for 400 μs and with a delay of 50 μs.

The results are given in the Table below, expressed in Δcps corresponding to the difference between the signal emitted by the sample at 665 nm with respect to the standard solution (serum without CEA).

| CEA ng/ml | AP Δcps | $(\alpha^{AP}, \beta^{AP})_3 L_C$ complex Δcps |
|---|---|---|
| 4.4 | 251 | 388 |
| 15.9 | 966 | 1670 |
| 118 | 6427 | 9804 |
| 236 | 9436 | 16232 |

The results show that the signal measured is larger for the phycobiliprotein-linker protein complex with respect to the phycobiliprotein alone.

Furthermore, it is noted that the ratio $DO_{650}/DO_{620} = 2.2$ which characterises said complex is constant within the limit of measurement errors for all the steps of the preparation of the conjugate, and very different from that of the AP (≈1,45).

This demonstrates the stability of the phycobiliprotein-linker peptide complex throughout the steps of purification and coupling which are carried out without any particular precautions with respect to that of the G15 AP conjugate.

I claim:

1. A fluorescent method of detecting and/or determining an analyte in a medium in which it may be present, characterised in that a phycobiliprotcin-linker peptide complex is used as a fluorescent tracer.

2. The method according to claim 1, characterised in that the phycobiliprotein of said phycobiliprotein-linker peptide complex is selected from phycocrythrin, phycoerythrocyanine, phycocyanine, allophycocyanine and allophycccyanine B.

3. The method according to claim 1 characterised in that the phycobiliprotein-linker peptide complex is extracted from a cyanobacterium selected from Mastigocladus Laminosus, Synechocystis 6701, Synechococcus, 6301, *Anabaena variabilis* and Nostoc spec.

4. The method according to claim 1, characterised in that the linker peptide of said phycobiliprotein-linker peptide complex is selected from the peptides $L_R$, $L_C$, $L_{RC}$ and $L_{CM}$.

5. The method according to claim 1, characterised in that the phycobiliprotein-linker peptide complex is selected from the complexes

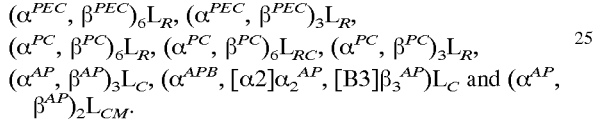

6. A homogenous fluorescent method of detecting and/or determining an analyte in a medium in which it may be present, by displaying the product of the reaction between the analyte and at least one corresponding receptor, consisting of:

1) adding to said medium a first reagent constituted of at least one receptor of said analyte,
2) adding a second reagent selected from the analyte or at least one of its receptors, one of said first reagent or said second reagent coupled with a flourescent donor compound constituted by a rare earth cryptate, chelate or macrocyclic complex and other reagent being coupled with a fluorescent acceptor compound, it being possible for the order of addition of the reagents to be the reverse order and, after excitation of the mixture by a source of light at the excitation wavelength of the fluorescent donor compound,
3) measuring the emission signal of the fluorescent acceptor compould, and
4) correlating the measured emission signal of the fluorescent acceptor compound to the presence and/or amount of analyte, characterised in that a phycobiliprotein-linker peptide complex is used as a fluorescent acceptor compound.

7. The method according to claim 6 which consists of an excess method, characterised in that it consists of:

1) adding to said medium containing the analyte sought after a first reagent constituted by at least one receptor of said analyte coupled with a fluorescent donor compound constituted by a rare earth cryptate, chelate or macrocyclic complex,
2) adding a second reagerit constituted by one or more other receptors of said analyte, said second reagent being coupled with a fluorescent acceptor compound constituted by a phycobiliprotein-linker peptide complex,
3) incubating said medium after each addition of reagents or after the addition of the second reagent,
4) exciting the resulting medium at the excitation wavelength of the fluorescent donor compound,
5) measuring the signal emitted by the fluorescent acceptor compound.

8. The method according to claim 6 consisting of a competitive method, characterised in that it consists of:

1) adding to said medium containing the analyte sought after a first reagent constituted by a receptor of said analyte, coupled with a fluorescent donor compound constituted by a rare earth cryptate, chelate or macrocyclic complex,
2) adding a second reagent constituted of the analyte coupled with a fluorescent acceptor compound constituted by a phycobiliprotein-linker peptide complex,
3) incubating said medium after each addition of reagents or after the addition of the second reagent,
4) exciting the resulting medium at the excitation wavelength of the fluorescent donor compound,
5) measuring the signal emitted by the fluorescent acceptor compound.

9. The method according to claim 6 consisting of a competitive method, characterised in that it consists of:

1) adding to said medium containing the analyte sought after a first reagent constituted by a receptor of said analyte, said receptor being coupled with a fluorescent acceptor compound constituted by a phycobiliprotein-linker peptide complex,
2) adding a second reagent constituted of the analyte coupled with a fluorescent donor compound constituted by a rare earth cryptate or chelate,
3) incubating said medium either after the addition of each reagent, or after the addition of the second reagent,
4) exciting the resulting medium at the excitation wavelength of he fluorescent donor compound,
5) measuring the signal emitted by the fluorescent acceptor compound.

10. The method according to any one of claims 6 to 9, characterised in that the first reagent and the second reagent are added simultaneously to the medium containing the analyte sought after.

11. The method according to any one of claims 6 or 7, characterised in that one sole receptor of the analyte is used which is coupled either with the fluorescent donor compound, or with the fluorescent acceptor compound.

12. The method according to any one of claims 6 to 9, characterised in that the fluorescent donor compound is a terbium or europium chelate, cryptate or macrocyclic complex.

13. The method according to any one of claims 6 to 9 characterised in that the fluorescent donor compound is an $Eu^{3+}$ chelate, cryptate or macrocyclic complex and the fluorescent acceptor compound is the $(\alpha^{AP}, \beta^{AP})_3 L_C$ complex.

14. A method of amplification of the emission signal of a rare earth cryptate or chelate used as fluorescent donor compound in a fluorescent assay according to claim 1, in which a fluorescent acceptor compound is also used, characterised in that the rare earth clyptate or chelate possesses a low overall quantum yield, and in that the quantum yield of radiative deactivation from the emission level of the rare earth is lower than the quantum yield of the acceptor being constituted by a phycobiliprotein-linker peptide complex.

15. The method according to claim 1, characterised in that the phycobiliprotein-linker peptide complex is used in combination with one or more different fluorescent tracers.

16. A fluorescent conjugate constituted of a phycobiliprotein-linker peptide complex covalently bound to one of the elements of a ligand/receptor specific binding pair.

17. The conjugate according to claim 16, characterized in that the phycobiliprotein of said phycobiliprotein-linker peptide complex is selected from phycoerythrin, phycoerythrocyanine, phycocyanine, allophycocyanine and allophycocyanine B.

18. The conjugate according to claim 16 or 17, characterized in that the linker peptide of said phycobiliprotein-linker peptide complex is selected from the peptides $L_R$, $L_C$, $L_{RC}$ and $L_{CM}$.

19. The conjugate according to one of claims 16 or 17, characterised in that the phycobiliprotein-linker peptide complex is selected from the complexes $(\alpha^{PEC}, \beta^{PEC})_6 L_R$, $(\alpha^{PEC}, \beta^{PEC})_3 L_R$,
$(\alpha^{PC}, \beta^{PC})_6 L_R$, $(\alpha^{PC}, \beta^{PC})_6 L_{RC}$, $(\alpha^{PC}, \beta^{PC})_3 L_R$,
$(\alpha^{AP}, \beta^{AP})_3 L_C$, $(\alpha^{APB}, [\alpha 2]\alpha_2^{AP}; [B3]\beta_3^{AP})L_C$ and $(\alpha^{AP}, \beta^{AP})_2 L_{CM}$.

20. The conjugate according to one of claims 16 or 17, characterised in that the phycobiliprotein-linker peptide complex is extracted from a cyanobacterium selected from Mastigoclodus Laminosus, Synechocystis 6701, Synechococcis 6301, *Anabaena variabilis* and Nostoc spec.

21. The conjugate according to claim 16, characterised in that the element of the ligand/receptor specific binding pair is a receptor.

22. The conjugate according to claim 16, characterised in that the element of the ligand/receptor specific binding pair is a ligand.

23. A flow cytometry method characterized by the use of the conjugate of claim 16 or 17.

24. The method of claim 6 wherein phycobiliprotein of said phycobiliprotein-linker peptide complex is selected from phycoerythrin, phycoerythrocyanine, phycocyanine, allophycocyanine and allophycocyanine B.

25. The method of claim 6 wherein said phycobiliprotein-linker peptide complex is extracted from a cyanobacterium selected from Mastigoclodus Laminosus, Synechocystis 6701, Synechococcus, 6301, *Anabaena variabilis* and Nostoc spec.

26. The method of claim 6 wherein the linker peptide of said phycobiliprotein-linker peptide complex is selected from the peptides $L_R$, $L_C$, $L_{RC}$ and $L_{CM}$.

27. The method of claim 6 wherein said phycobiliprotein-linker peptide complex is selected from the complexes $(\alpha^{PEC}, \beta^{PEC})_6 L_R$, $(\alpha^{PEC}, \beta^{PEC})_3 L_R$,
$(\alpha^{PC}, \beta^{PC})_6 L_R$, $(\alpha^{PC}, \beta^{PC})_6 L_{RC}$, $(\alpha^{PC}, \beta^{PC})_3 L_R$,
$(\alpha^{AP}, \beta^{AP})_3 L_C$, $(\alpha^{APB}, \alpha 2^{AP}, B3^{AP})L_C$ and $(\alpha^{AP}, \beta^{AP})_2 L_{CM}$.

28. The conjugate of claim 21 wherein said receptor is a cell receptor or an antibody.

29. The conjugate of claim 22 wherein said ligand is an analyte.

* * * * *

UNITED STATES PATENT AND TRADEMARK OFFICE
CERTIFICATE OF CORRECTION

PATENT NO. : 6,020,212
DATED : February 1, 2000
INVENTOR(S) : Gerard Mathis

It is certified that error appears in the above-indentified patent and that said Letters Patent is hereby corrected as shown below:

Column 1, line 38; "c(ore " should read - core -

Column 1, line 45; "lcicalisation" should read - localisation -

Column 1, line 60; "fliiorimetry" should read - fluorimetry -

Column 1, line 65; "phycobil-iprotein" should read
    - phycobiliprotein-linker -

Column 2, line 7, "pejptide" should read - peptide -

Column 3, line 33; "metheds" should be - methods -

Column 4, line 48; "e arth" should read - earth -

Column 6, line 42; "sulphio-" should be - sulpho -

Column 7, line 33; "Pharnacia" should read - Pharmacia -

Column 9, line 61; "reagerit" should read - reagent -.

Signed and Sealed this

Twentieth Day of February, 2001

Attest:

NICHOLAS P. GODICI

Attesting Officer        Acting Director of the United States Patent and Trademark Office